(12) United States Patent
Stephens

(10) Patent No.: US 8,706,424 B2
(45) Date of Patent: Apr. 22, 2014

(54) SYSTEM FOR ESTIMATING A GAS CONCENTRATION IN A MIXED ATMOSPHERE

(75) Inventor: Scott Stephens, Carefree, AZ (US)

(73) Assignee: H2Scan Corporation, Newport Beach, CA (US)

( * ) Notice: Subject to any disclaimer, the term of this patent is extended or adjusted under 35 U.S.C. 154(b) by 1284 days.

(21) Appl. No.: 12/495,735

(22) Filed: Jun. 30, 2009

(65) Prior Publication Data

US 2010/0332147 A1     Dec. 30, 2010

(51) Int. Cl.
 *G06F 19/00* (2011.01)
(52) U.S. Cl.
 USPC .............................. 702/24; 73/23.32; 123/672
(58) Field of Classification Search
 USPC .............................. 702/24; 73/23.32; 123/672
 See application file for complete search history.

(56) References Cited

U.S. PATENT DOCUMENTS

| 5,279,795 | A  | 1/1994  | Hughes       |
| 5,535,135 | A  | 7/1996  | Bush         |
| 7,228,725 | B2 | 6/2007  | Salter et al.|
| 7,249,490 | B2 | 7/2007  | Pendergrass  |
| 2003/0233212 | A1 | 12/2003 | Von Drasek |
| 2005/0189238 | A1 | 9/2005  | Howard et al.|

OTHER PUBLICATIONS

PCT Notification of Transmittal of the International Search Report and The Written Opinion of the International Searching Authority, or the Declaration, in PCT/US2010/040533, dated Feb. 10, 2011.

J. Qu, Y. Chai, S.X. Yang: "A real-time de-noising algorithm for e-noses in a wireless sensor network", SENSORS, vol. 9, Feb. 11, 2009, pp. 895-908, XP002618272, the whole document.
M. Johansson, I. Lundstrom, and L.-G. Ekedahl, Bridging the Pressure Gap for Palladium Metal-Insulator-Semiconductor Hydrogen Sensors in Oxygen Containing Environments, Journal of Applied Physics, Jul. 1, 1998, pp. 44-51, vol. 84, No. 1.
Joakim Fogelberg, Lars-Gunnar Petersson, Kinetic Modelling of the H2-02 Reaction on Pd and of its Influence on the Hydrogen Response of a Hydrogen Sensitive Pd Metal-Oxide-Semiconductor Device, Elsevier Science B.V., Surface Science 350, 1996, pp. 91-102.
J. Fogelberg, M. Eriksson, H. Dannetun, and L.-G. Petersson, Kinetic Modeling of Hydrogen Adsorption/Absorption in Thin Films on Hydrogen-Sensitive Field-Effect Devices: Observation of Large Hydrogen-Induced Dipoles at the Pd-SiO2 Interface, Journal of Applied Physics, 78(2) Jul. 15, 1995, pp. 988-996.

(Continued)

*Primary Examiner* — Jonathan C. Teixeira Moffat
*Assistant Examiner* — Hien Vo
(74) *Attorney, Agent, or Firm* — McAndrews, Held & Malloy, Ltd.

(57) ABSTRACT

A system for estimating gas concentrations in a mixed atmosphere includes (a) a plurality of sensors for providing a set of measurements, at least one of the sensors sensitive to an internal concentration of hydrogen; and (b) a processor for receiving the set of measurements and for executing a sequential estimation filter that includes a plurality of states having a corresponding set of values. The processor responsively adjusts at least a portion of the set of values in response to the set of measurements. The plurality of sensors can include a resistive sensor and a capacitive gas sensor, both of which are sensitive to hydrogen concentration. The plurality of states can include states representative of hydrogen pressure in the mixed atmosphere, hydrogen concentration in a bulk material of at least one of the sensors, and hydrogen concentration in an interface layer of at least one of the sensors.

20 Claims, 4 Drawing Sheets

(56) References Cited

OTHER PUBLICATIONS

David L. Griscom, Diffusion of Radiolytic Molecular Hydrogen as a Mechanism for the Post-Irradiation Buildup of INterface States in SiO2-on-Si Structures, Journal of Applied Physics 58 (7), Oct. 1, 1985, pp. 2524-2533.

L. Tsetseris and S. T. Pantelides, Migration, Incorporation, and Passivation Reactions of Molecular Hydrogen at the Si-SiO2 Interface, The American Physical Society, Physical Review B 70, 245320, 2004, pp. 245320-1-245320-6.

R. C. Hughes, W. K. Schubert, and R. J. Buss, Solid-State Hydrogen Sensors Using Palladium-Nickel Alloys:Effect of Alloy Composition on Sensor Response, The Electrochemical Society, Inc., vol. 142, No. 1, Jan. 1, 1995, pp. 249-254.

R. C. Hughes, P. A. Taylor, A. J. Ricco, and R. R. Rye, Kinetics of Hydrogen Absorption: Catalytic Gate MIS Gas Sensors on Silicon, The Electrochemical Society, Inc., J. Electrochem. Soc., vol. 136, No. 9, Sep. 1989, pp. 2653-2661.

Anette Salomonsson, Mats Eriksson, and Helen Dannetun, Hydrogen Interaction With Platinum and Palladium Metal-Insulator-Semiconductor Devices, Journal of Applied Physics 98, Jul. 2005, pp. 014505-1-014505-10.

M. Eriksson, I. Lundstrom, and L.-G. Ekedahl, A Model of the Temkin Isotherm Behavior for Hydrogen Adsorption at Pd-SiO2 Interfaces, Journal of Applied Physics 82 (6), Sep. 15, 1997, pp. 3143-3146.

PCT International Bureau, Notification Concerning Transmittal of International Preliminary Report on Patentability and Report, in International application No. PCT/US10/040533, dated Jan. 12, 2012. (8 pages).

SYSTEM FOR ESTIMATING A GAS CONCENTRATION IN A MIXED ATMOSPHERE

FIELD OF THE INVENTION

The present invention relates generally to the estimation of gas concentrations, and in particular to the detection and measurement of hydrogen gas in mixed atmospheres.

BACKGROUND OF THE INVENTION

Solid-state gas sensors are sensitive to the partial pressure (herein, "pressure") or concentration of one or more gasses in a mixed atmosphere. Some types of solid-state gas sensors include those described in U.S. Pat. No. 5,279,795. These sensors are sensitive to one or more types of gas (for example, hydrogen ($H_2$) and oxygen ($O_2$)). Solid-state gas sensors are designed to provide measurements from which a gas pressure can be estimated. The sensors can also be employed to detect the rate of change in pressure, in order to infer the effects being monitored and measured.

For a given application, a gas sensing system can be designed to detect the pressure of a target gas (for example, $H_2$). In addition to the target gas pressure, however, there are factors that can influence a gas sensor's measurements. For example, non-target gasses can influence the measurements. Additionally, other factors such as temperature and humidity can have an impact. Solid-state gas sensors can also have a delayed response to stimuli. For example, if there is a sudden target gas pressure change, the sensor might take from tenths to thousandths of seconds to reach near steady-state response at the new pressure.

Different approaches can be employed to mitigate the impact of these factors. For example, to reduce the effects of temperature, a heater can be employed to keep the sensor within a specified temperature range. Further, the gas sensing system can be calibrated over this temperature range to compensate for the effects of temperature. As another example, to reduce the impact of non-target gasses, a gas sensing system can be calibrated for a desired operating environment. For instance, the sensor response to the target gas (for example, $H_2$) can be measured in air and the system calibrated accordingly. In such an example, an assumption can be made as to the pressure of non-target gasses and humidity. Humidity or water vapor, a gas, may be characteristic of common environmental conditions compared to other gasses, and may interfere with a target gas detection and measurement system and the gas sensing system could be calibrated according to this specific operating condition. As another example, to mitigate a delayed response of the sensor, a user can observe the direction of change in the sensor signal as an indicator of changes in target gas pressure, quasi-quantitatively, the direction of change being correlated with the developing phenomena.

The present gas sensing system can operate flexibly over a larger range of operating conditions by dynamically accounting for influencing factors.

SUMMARY OF THE INVENTION

A system for estimating gas concentrations in a mixed atmosphere comprises:
 (a) a plurality of sensors for providing a set of measurements, at least one of the sensors sensitive to a concentration of hydrogen internal to said at least one of the sensors; and
 (b) a processor for receiving the set of measurements, and for executing a sequential estimation filter comprising a plurality of states, the plurality of states having a corresponding set of values.

In operation, the processor responsively adjusts at least a portion of the set of values in response to the set of measurements.

In a preferred embodiment of the system, the plurality of sensors comprises a resistive sensor and a capacitive sensor. The plurality of sensors preferably further comprises a temperature sensor.

In a preferred embodiment, the plurality of states preferably comprises states representative of a hydrogen pressure in the mixed atmosphere, a concentration of hydrogen in a bulk material of at least one of the sensors, and a concentration of hydrogen in an interface layer of at least one of the sensors. The plurality of states preferably further comprises states representative of a concentration of oxygen on a surface of one of the sensors, and an oxygen pressure in the mixed atmosphere.

In a preferred embodiment of the system, at least a portion of the state values include initial state values.

In a further preferred embodiment of the system, the sequential estimation filter comprises a Kalman filter.

A method for estimating gas concentrations in a mixed atmosphere, the method comprises:
 (a) receiving at a first time, a first set of measurements from a plurality of sensors, at least one of the sensors sensitive to a concentration of hydrogen internal to said at least one of the sensors;
 (b) processing the first of the set of measurements in a sequential estimation filter to adjust a set of state values;
 (c) receiving at a second time a second set of measurements from the plurality of sensors; and
 (d) processing the second of the set of measurements in the sequential estimation filter to further adjust the set of state values.

In a preferred embodiment of the method, the plurality of sensors comprises a resistive sensor and a capacitive sensor. The plurality of sensors can further comprise a temperature sensor.

In a preferred embodiment of the method, the set of state values preferably comprises values representative of a hydrogen pressure in the mixed atmosphere, a concentration of hydrogen in a bulk material of at least one of the sensors, and a concentration of hydrogen in an interface layer of at least one of the sensors. The set of state values preferably further comprises values representative of a concentration of oxygen on a surface of at least one of the sensors, and an oxygen pressure in the mixed atmosphere.

In a preferred embodiment of the system, at least a portion of the state values is initialized.

In a further preferred embodiment of the system, the sequential estimation filter comprises a Kalman filter.

A further method for estimating gas concentrations in a mixed atmosphere, the method comprises:
 (a) receiving at a first time, a first set of measurements from a plurality of sensors;
 (b) processing the first of the set of measurements in a sequential estimation filter to adjust a set of state values;
 (c) receiving at a second time a second set of measurements from the plurality of sensors; and
 (d) processing the second of the set of measurements in the sequential estimation filter to further adjust the set of state values.

In operation, the set of state values comprises at least three state values.

In a preferred embodiment of the foregoing method, the sequential estimation filter comprises a Kalman filter. The at least three state values preferably comprise values representing a hydrogen pressure in the mixed atmosphere, a concentration of hydrogen in a bulk material of at least one of the sensors, and a concentration of hydrogen in an interface layer of at least one of the sensors.

In another preferred embodiment of the foregoing method, the set of state values comprises at least five state values. The at least five state values preferably comprise values representative of a hydrogen pressure in the mixed atmosphere, a concentration of hydrogen in a bulk material of at least one of the sensors, and a concentration of hydrogen in an interface layer of at least one of the sensors, a concentration of oxygen on a surface of at least one of the sensors, and an oxygen pressure in the mixed atmosphere.

In the foregoing method, the plurality of sensors comprise a resistive sensor and a capacitive sensor.

BRIEF DESCRIPTION OF THE DRAWING(S)

DETAILED DESCRIPTION OF PREFERRED EMBODIMENT(S)

Figure 1:
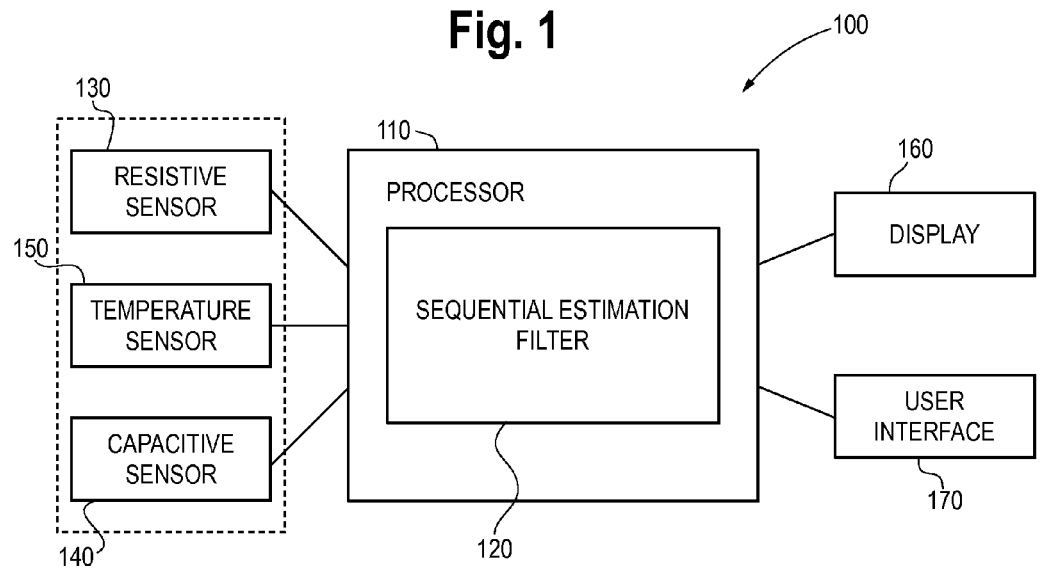
FIG. 1 shows a block diagram of a system for measuring the pressure of one or more gasses, in accordance with an embodiment of the present system.

FIG. 1 shows a block diagram of a system 100 for measuring the pressure of one or more gasses, in accordance with an embodiment of the present system. System 100 includes a processor 110 that can be coupled (for example, logically or physically) to sensors 130, 140, and 150. Processor 110 can also be coupled to other components, such as display 160 and user interface 170. Sensors 130, 140, and 150 can be in a mixed atmosphere 180. Mixed atmosphere 180 can have two or more gasses having variable concentrations. The gasses can include, for example, $H_2$ and $O_2$. The mixed atmosphere can include one or more other constituent gasses, such as $H_2O$, CO, $H_2S$, $Cl_2$, and $N_2$.

Processor 110 can include sub-processing units, such as a digital signal processor. Processor 110 is capable of executing a set of instructions from a computer readable medium that effects gas measurement methods, such as the ones shown in FIGS. 5 and 6, described below. The processor can receive input data from user interface 170, and can provide displayable data to display 160.

Resistive sensor 130 and capacitive sensor 140 may be sensitive to the presence of the target gas (for example, $H_2$). Sensors 130 and 140, either by themselves or in combination, are capable of indicating variations in the partial pressure of the target gas. Temperature sensor 150 is capable of detecting the temperature of mixed atmosphere 180 and/or sensors 130 and 140.

Figure 2:
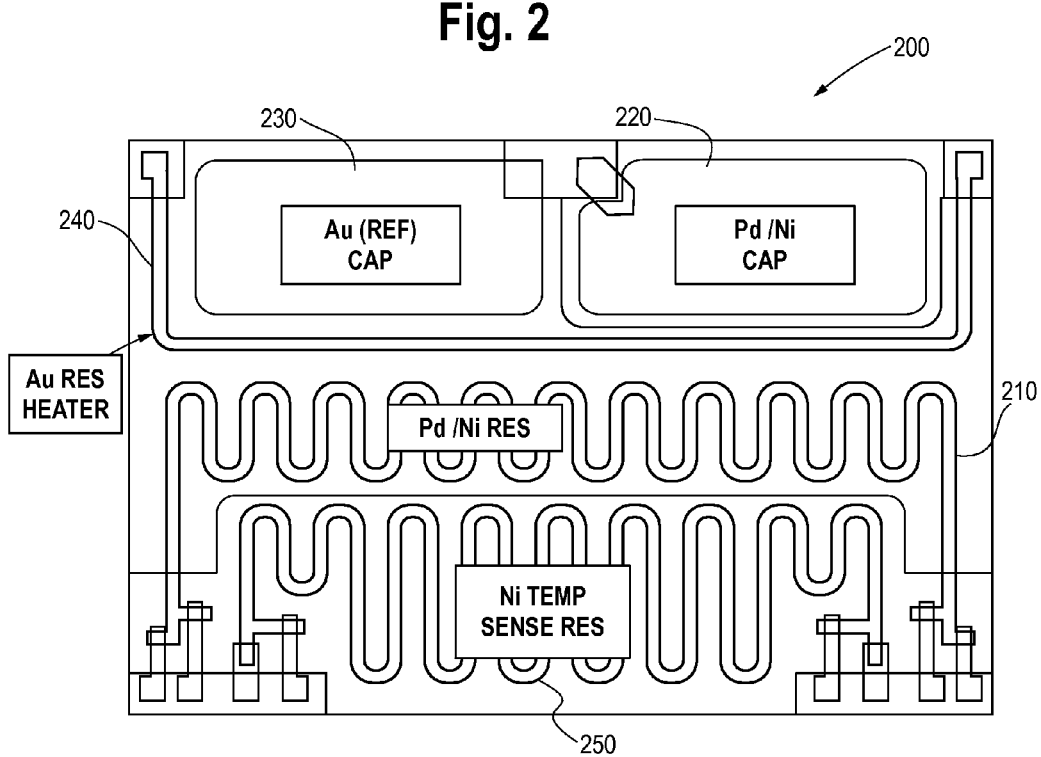
FIG. 2 shows gas sensors, in accordance with an embodiment of the present system.

Turning to FIG. 2, an exemplary configuration of gas sensors 200 is shown, in accordance with an embodiment of the present system. Configuration 200 includes resistive sensor 210, capacitive sensor 220, and temperature sensor 250 (similar to sensors 130, 140, and 150). The configuration also includes a heater 220 and reference capacitor 230. Temperature sensor 250 can include nickel (Ni) and can be a resistor (for example, 120 nm thick with trace measurements of 2×500 mil). Sensor 250 can also be coated with Alumina, to provide a protective barrier. Heater 220 is capable of controlling the temperature of the sensing environment. Heater 220 can include gold (Au), and can be a resistive heater (for example, 400 nm thick with trace measurements of 2×200 mil). The heater may be employed to control the temperature of a substrate, by passing current through this heating element in a closed-loop with the temperature sensor. A relatively stable operating temperature is often desirable. Reference capacitor 230 can include Au, and can be, for example, 400 nm thick, with trace measurements of 56×25 mil.

The reference capacitor is one technique, for example, of establishing a baseline capacitance for the Hydrogen sensing capacitor. The capacitor may employ a Pd—Ni alloy, for example, for catalyzing $H_2$ molecules and creating an electric field proportional to the number of such Hydrogen atoms. Because capacitance may be a function of the voltage applied (among other parameters) and the rate at which the voltage is applied to the capacitor, a reference capacitor that is substantially similar in capacitance (for example, dimensions, conductivity, or dielectric constant) can be used. A reference capacitor, which may employ a non-catalytic Au metal and hence not energized by Hydrogen atoms, may be employed as a reference to measure the change induced by the presence of Hydrogen. Relatively low levels of Hydrogen concentration and a saturation level may be exponential in charge concentration at the interface layer between the insulator material, the conductive layer and the semiconductor surface.

Resistive sensor 210 and capacitive sensor 220 can have varying resistance and capacitance respectively according to concentrations of the target gas within the sensors. Resistive sensor 210 can include a palladium-nickel alloy (PdNi), and can be, for example, 80 nm thick, with trace measurements of 2×500 mil. Resistive sensor 210 can involve processes similar to those disclosed in R. C. Hughes et al., Solid-State Hydrogen Sensors Using Palladium-Nickel Alloys: Effect of Alloy Composition on Sensor Response, J. Electrochem. Soc., Vol. 142, No. 1, January 1995. Resistive sensor 210 can be sensitive to relatively higher concentrations of $H_2$, such as a few 10 s of parts per million (ppm), up to 100% concentration. The concentration of H atoms in a PdNi lattice (described in more detail below) can increase resistivity. For example, resistance can linearly increase in proportion to the levels of H in the PdNi lattice, which in turn is related to gaseous $H_2$ pressure as that described by Sievert's law. Other elements, such as $O_2$ can enter the PdNi lattice and create a lower limit on resistance.

Capacitive sensor 220 can include PdNi, and can be, for example, 80 nm thick with trace measurements of 56×25 mil. Configuration 200 can also include a semiconductor layer on the bottom, such as a 22 um n-type silicon wafer. The configuration of gas sensors 200 can also include an insulator/dielectric, such as a 65 nm layer of Silicon Nitride ($Si_3N_4$) on a 35 nm layer of silicon dioxide ($SiO_2$). The operation of capacitive sensor 220 can involve processes similar to those described in Bridging the Pressure Gap for Palladium Metal-Insulator-Semiconductor Hydrogen Sensors in Oxygen Containing Environments, M. Johansson et al., Journal of Applied Physics, Vol. 84, July 1998. Capacitive sensor 220 is sensitive to relatively low concentrations of $H_2$, such as 10 ppm to around 2-4% concentration. In some instances, it may be preferable to keep H out of the PdNi lattice—since it can take a relatively long time for the H to get out of the lattice. In such a case, it can be preferable for the mixed atmosphere to include $O_2$.

Figure 3:
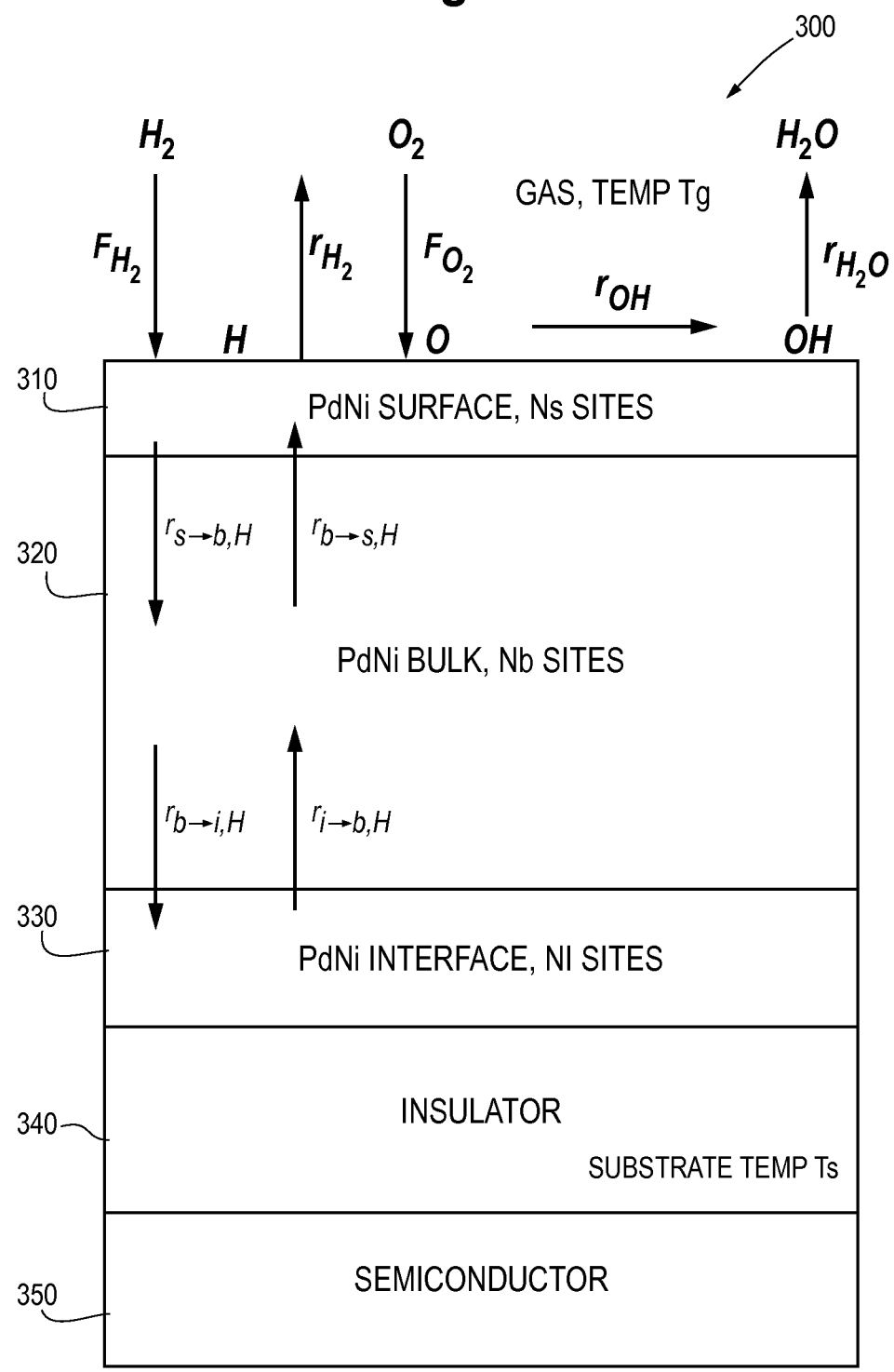
FIG. 3 shows a lattice for use in one or more gas sensors, in accordance with an embodiment of the present system.
Figure 4:
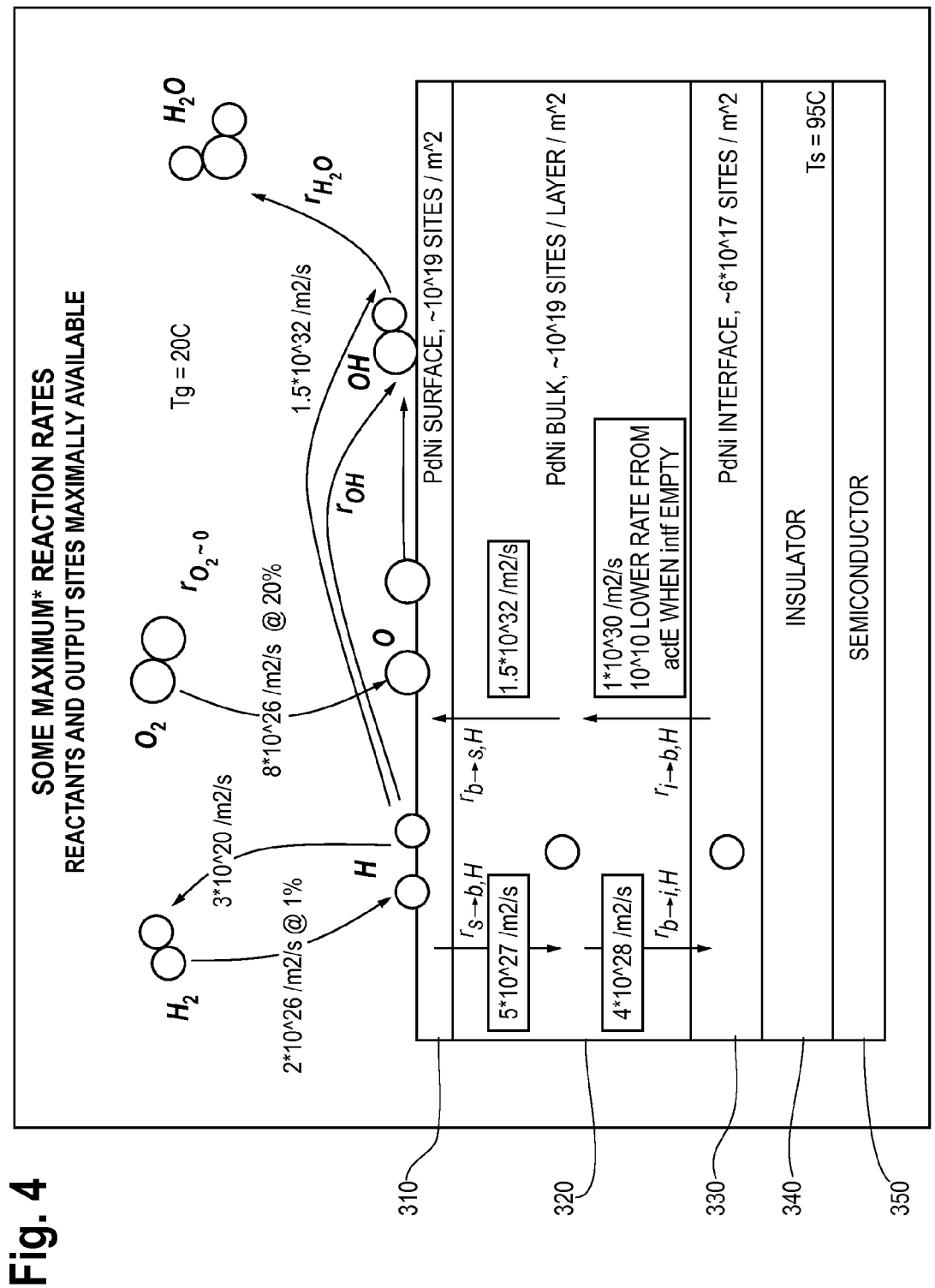
FIG. 4 shows a lattice for use in one or more gas sensors, in accordance with an embodiment of the present system.

Turning to FIGS. 3 and 4, a lattice 300 for use in one or more gas sensors is shown, in accordance with an embodiment of the present system. Lattice 300 can be employed to implement both resistive sensor 210 and capacitive sensor 220. Lattice 300 can include a PdNi surface 310, a PdNi bulk material 320, a PdNi interface layer 330, an insulator 340, and a semiconductor 350. All of these portions may not be necessary. For example, to implement resistive sensor 210, it may not be necessary to provide layers 330 or 340.

An atmosphere of gases is shown as a mixture (at temperature $T_g$) of $H_2$, $O_2$, and $H_2O$ above surface 310 (at temperature $T_s$). The gases can dissociate on the surface to form H and O (which become OH and $H_2O$ and leaves the surface, as described in more detail below). Hydrogen can permeate bulk material 320 down to interface layer 330 above insulator 340, and forms a dipole layer which causes a voltage shift in the capacitor's C-V curve (for example, when lattice 300 is implemented in a capacitive sensor). The H in bulk material 320 can add scattering centers, which can increase the resistance of the bulk material (for example, when lattice 300 is implemented in a resistive sensor).

The rate at which gases hit the surface can be given by the molecular flux $F_X$, in units of molecules/m2/s:

$$F_X = \frac{pX}{\sqrt{2\pi m_X k_B Y_g}}$$

$$X = \{H_2, O_2\}$$

where $m_x$ is the mass of the molecule (kg), kB is Boltzmann's constant (J/K), $T_g$ is the temperature of the gas (K), and pX is the partial pressure of the gas constituent (Pa).

The rate at which this flow of molecules adsorb or stick to surface 310 can be proportional to a "sticking factor" S (for example, 1 for $H_2$, and 0.8 for $O_2$) and the fraction of surface 310 which may be capable of accepting that molecule. Surface 310 can have a number of sites $N_s$, in units of/m², which atoms can occupy. Each gas constituent can occupy a number of these sites mX. For H, this can be unity, but for O or OH it has been assumed in the literature to be 4.

At a given time, let the surface concentration of each constituent be given by $n_{sX}$, in units of/m²:

$$n_{sX} X = \{H, O, OH\}$$

The total number of surface sites occupied is $n_s$, in units of/m², and the total available (vacant) can be $n_{sA}$, in units of/m², and can be given by:

$$n_s = \sum_X m_X \cdot n_{sX}$$

$$n_{sA} = N_s - n_s$$

The fractional occupancy (normalized by the number of sites) $\theta_s$ and the available (vacancy) fraction $\theta_{sA}$ can be given by:

$$\theta_s = \frac{n_s}{N_s}$$

$$\theta_{sA} = 1 - \theta_s = 1 - \frac{n_s}{N_s}$$

Atomic or molecular concentrations can also be expressed in this normalized coverage form relative to the number of sites available for the particular constituent.

It may be desired to determine the rate at which a gas adsorbs or sticks to the surface. To stick to the surface, a molecule may require a certain number of adjacent vacancy sites. For example, $H_2$ can require 2*mH or 2 sites adjacent to stick. The probability of any one site being available (vacant) may be $\theta_s$. The probability of n adjacent sites may be $(\theta_{sA})^n$. So the rate of each gas constituent onto the surface given a particular surface occupancy state can be given by:

$$r_{X_2 \to sX} = 2 \cdot F_{X_2} S_{X_2} \cdot \theta_{sA}^{2mX}$$

Note that for $O_2$, the power of the fraction of sites available may be 8, since 8 adjacent sites may be needed for one $O_2$ molecule, as implicated by the processes characterized by Langmuir reactions.

The rate that gases are evolved from the surface can depend on the rate at which components collide and the activation energy of the reaction. The collision rate can be given by the product of the concentration of each component and a frequency factor v, (for example, $10^{13}$/s). So the rate generation of gases can be given by:

$$r_{sX \to X_2} = v N_s \left(\frac{n_{sX}}{N_s}\right)^2 e^{-E_{sX \to X_2}/k_B T_s}$$

The activation energy can be non-negative, and can express an energy to get out of the local energy well and not the total energy liberated in case of net energy release. So some reactions might be like "falling off a cliff," which can then have an activation energy of zero.

On the surface, and into the bulk material, reactions can follow the same form, except also dependent on the number of available sites the reaction can take place into:

$$r_{sH,sO \to sOH} = v \cdot N_s \left(\frac{n_{sH}}{N_s}\right)\left(\frac{n_{sO}}{N_s}\right)\theta_{sA} \cdot e^{-E_{sH,sO \to sOH}/k_B T_s}$$

$$r_{sH \to bH} = v \cdot N_s \left(\frac{n_{sH}}{N_s}\right)\left(1 - \frac{n_{sH}}{N_b}\right) e^{-E_{sH \to bH}/k_B T_s}$$

$$r_{bH \to sH} = v \cdot N_s \left(\frac{n_{bH}}{N_b}\right)\left(1 - \frac{n_{sH}}{N_s}\right) e^{-E_{bH \to sH}/k_B T_s}$$

Note that when flow is between two states with different densities of sites, the smaller number of sites can limit the rate, for example, when $N_s$ is less than $N_b$.

Water can be generated directly into the atmosphere, without an intermediate state or required activation energy:

$$r_{sH,sOH \to H_2O} = v N_s \left(\frac{n_{sH}}{N_s}\right)\left(\frac{n_{sOH}}{N_s}\right) e^{-E_{sH,sOH \to H_2O}/k_B T}$$

Finally, reactions from the bulk material into the interface layer may be a special case, since the energy of the available interface layer sites can depend on the interface layer coverage:

$$E_{iH \to bH} = E_{iH \to bH,0}\left(1 - a\frac{n_{iH}}{N_i}\right)$$

$$r_{iH \to bH} = vN_i\left(\frac{n_{iH}}{N_i}\right)\left(1 - \frac{n_{bH}}{N_b}\right)e^{-E_{iH \to bH}/k_B T_s}$$

$$r_{bH \to iH} = vN_i\left(\frac{n_{bH}}{N_b}\right)\left(1 - \frac{n_{iH}}{N_i}\right)e^{-E_{bH \to iH}/k_B T_s}$$

The interface layer energy constant can be roughly unity. For the case of $H_2$ and $O_2$ above the device, the full set of state rate equations can be summarized as:

$$\dot{n}_{sH} = +r_{H_2 \to sH} - r_{sH \to H2} - r_{sH,sO \to sOH} - r_{sH,sOH \to H_2O} + r_{bH \to sH} - r_{sH \to bH}$$

$$\dot{n}_{sO} = +r_{O_2 \to sO} - r_{sO \to O2} - r_{sH,sO \to sOH}$$

$$\dot{n}_{sOH} = +r_{sH,sO \to sOH} - r_{sH,sOH \to H_2O}$$

$$\dot{n}_{bH} = +r_{sH \to bH} - r_{bH \to sH} + r_{iH \to bH} - r_{bH \to iH}$$

$$\dot{n}_{iH} = +r_{bH \to iH} - r_{iH \to bH}$$

The concentrations n can be expressed as normalized quantities in the form of fractional occupancies/theta by dividing by the total site number for the particular constituent N. For instance, the fractional occupancy for the interface layer/theta i=ni/Ni.

There may also be other considerations to account for. For example, structural defects (for example, grain boundaries, voids, etc.) can cause higher binding energy (for example, 0.2-0.5 eV). As another example, CO can occupy surface sites, thereby reducing $N_s$.

Figure 5:
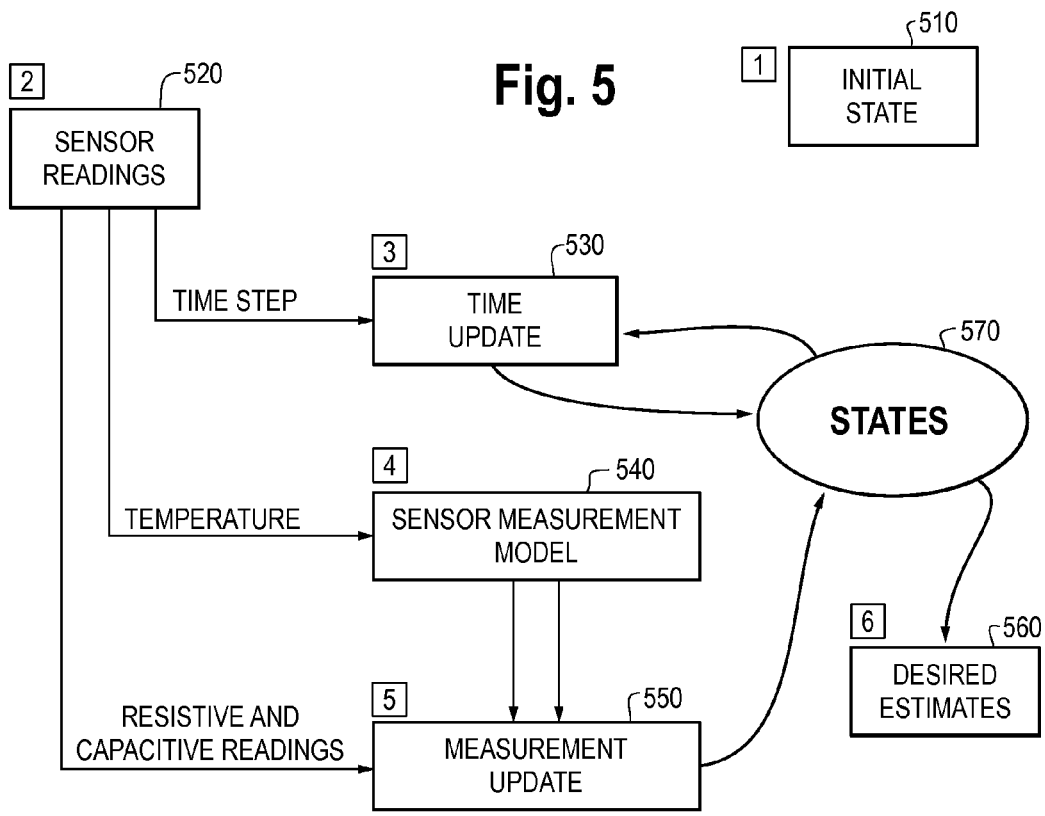
FIG. 5 shows a flow chart for measuring a pressure of one or more gasses, in accordance with an embodiment of the present system.

FIG. 5 shows flow chart 500 for measuring the pressure of one or more gasses, in accordance with an embodiment of the present system. The steps can be performed, for example, by a system, such as system 100. The process depicted in flow chart 500, or a portion thereof, can be performed by one or more processing units. The process depicted in flow chart 500, or a portion thereof, can be performed by software, hardware, and/or firmware. Flow chart 500, or a portion thereof, can also be expressed through a set of instructions, at least in part, stored on one or more computer-readable storage media, such as RAM, ROM, EPROM, EEPROM, optical disk, magnetic disk, magnetic tape, and/or the like.

At step 570, a set of sequential estimation filter state elements can be maintained and updated to estimate the pressure of external gasses, and other relevant variables as further described herein. The estimation filter state elements can include the parameters to be estimated (for example, gas pressures above the sensor) as well as a description of conditions on the surface and within the sensor (for example, concentrations of atoms adsorbed onto the surface and within the bulk material of the sensor). The state elements can also include the uncertainty in estimates. The state elements may be a representation of an N-dimensional probability distribution. For some types of state-space estimation filters, the distribution can be described by the second moment of the probability distribution—for example, a mean vector with a covariance matrix. The sequential estimation filter can be, for example, a Kalman filter.

At step 510, initial values for the estimation filter state elements can be provided, if known. The initial state values can represent the parameters to be estimated (for example, gas pressures above the sensor), or conditions on the surface or within the sensor (for example, concentrations of atoms adsorbed onto the surface or within the bulk material of the sensor). The initial state values can also include uncertainties in the estimates, if known. In general, the state can be a representation of an N-dimensional probability distribution. For some classes of state-space estimation filters, the distribution can be described by the second moment of the probability distribution—for example, a mean vector with a covariance matrix.

At step 520, sensor readings can be obtained, for example, through gas sensors 200 and any conditioning or associated circuitry. The sensors (for example, resistive, capacitive, and temperature sensors) can provide analog voltages at a given time interval. The voltages can be converted to digital values by one or more analog-to-digital converters to supply to a processor for further processing as described herein.

At step 530, a time is updated according to a time step and relevant dynamics. Some examples of dynamics are external gas pressures. For example, dynamics can include an estimation of how fast an external gas pressure can change, or the likely range of pressures. The time step between measurements can be employed by the filter to propagate forward one or more states. State elements that represent rates can be scaled by time and employed to increment their corresponding estimate terms. Zero-seeking estimates, such as generalized Gauss-Markov terms, can be updated by forgetting factors based on corresponding time constants. The state elements can be allowed to change in view of process noise, such that uncertainty in elements can grow (or at least not shrink) during the time update step. For example, Gauss-Markov processes can grow in uncertainty based on time constants and steady-state uncertainty. As another example, random-walk processes can increase uncertainty variance (for example, in proportion to time). For instance, an external gas pressure might be modeled as a random-walk process that is allowed to change 1% per minute or 2% every 4 minutes.

Process noise during the time update process can cause an estimate to be non-constant. If no process noise is added, the uncertainty in the state can decrease over time—for example, such as estimating one constant value for the time span during which measurements were taken. Some state terms can change in accordance with physical rate power laws in chemical reactions. For example, rates can be proportional to the concentration of reactants, such as water forming reactions of H and O on a catalytic surface. As another example, rates can also be proportional to the number of sites available for the reaction to take place. This can include transitional state elements, such as the number of available sites for a transition from bulk material to surface.

When some reactants take multiple reaction sites, there can be a power law in the number of sites required—for example, according to a generalized Langmuir reaction. For example, if M adjacent sites are required for a reaction—such as a gas molecule sticking on a catalytic surface—the probability of finding coterminous sites can be a power law according to the concentration of available sites. Reaction rates can also scale by Boltzmann factors—for example, exponential scaling in reaction activation energy normalized by temperature energy.

At step 540, a sensor measurement model can be applied. The sensor model can be employed to predict sensor measurements from the current state. In addition to the resistive and capacitive sensor readings, the model can receive a temperature measurement as an input. For the resistive sensor, the resistance measured can be correlated with both the gas adsorbed on the surface and the gas absorbed into the bulk material. Resistance can also change as a function of temperature. For the capacitive sensor, gas absorbed onto the metal-insulator interface layer can cause a dipole layer and a corresponding voltage shift, which can be measured by shifts in, for example, C-V type curves. Since there can be a functional relation between the state and measurement, uncertainty in state can also map to an uncertainty in measurement prediction.

At step 550, the measurement prediction error can be employed to adjust the state. For example, comparing the measurement to the measurement prediction, and using the relative confidence level in both the measurement and the prediction, the measurement error can be associated with a prediction error, which in turn can be mapped to a most likely state error based on the measurement-to-state sensitivity (for example, for a Kalman filter, this can be the Jacobian). The new information in the form of a measurement with some level of certainty can reduce the state uncertainty in kind. Thus, while the time update step can increase the uncertainty, the measurement update step can decrease the uncertainty.

At step 570, the external gas pressures and internal sensor concentrations, and uncertainties thereof can be maintained in a set of elements. The elements can be updated with new measurements, and can be accessed through step 560 for sensor processing outputs, and provision to a user or further processing and/or display. One state element can be the target gas pressure. Other elements can include estimation of other gas pressures, and other estimated values as described herein.

There are various approaches for implementing flow chart 500, or at least a portion thereof. For example, it is possible to employ a Kalman filter, or a relatively simplified version thereof. In one such case, if the R and C response times to a relatively sudden change in $H_2$ pressure are known or can be estimated, then a Kalman filter can be employed to estimate the underlying $H_2$ level by predicting the direction in which the R and C values are heading. To further illustrate, the state for this approach can have 3 terms: $H_2$ pressure, and current slowly-changing estimates of R and C. The Kalman filter can employ the steady-state lookup tables, and can employ differences between predicted R and C and measured values to (a) adjust the predictions of R and C in the state, in a manner that matches the actual response delay seen from these sensors, and b) force the estimate of $H_2$ to a level that is consistent with the current change in R and C.

As another approach, it is possible to elaborate the Kalman filter using modeling of physical processes. For example certain responses in R and C measurements can be approximated by using physical models, such as Langmuir processes. Langmuir processes can represent how rates of change slow down in response to a diminishing number of sites available to the reaction. For example, the rates can slow down in response to overall site availability on the surface of the sensor, contiguous site availability on the surface, or having more than one input to the reaction (for example, the rate at which $H_2$ forms off of a surface can be related to the probability of two H atoms being available for the reaction, and the probability becomes proportional to the square of the H concentration). In general, these physical processes can be modeled with either simple exponential responses, or exponential responses in which time constants may be adjusted using concentrations of atoms in certain parts of the sensor. Atom concentrations can be employed in this modeling, the state count used by the Kalman filter can increase to accommodate the use of these concentrations.

One example is a 5 element state Kalman filter that models the concentration of H atoms in the Pd bulk material, H atoms on the capacitor interface layer, surface oxygen, as well as the external gas pressures of $H_2$ and $O_2$.

As yet another approach, the Kalman filter can be further elaborated. Similar to the 5-element state Kalman filter, a 7-element state model can be employed to reflect additional physical processes, such as the surface concentration of H atoms, and OH molecules. These are only a few examples of approaches. As a further approach, the sequential estimation filter can account for impurities in the Pd bulk material can add H sites with high binding energy. Under this approach, there can be more than one bulk material H concentration, and it is possible to track concentrations at each type of binding site, and each of these types can have different time constants for releasing the bound H. As yet another approach, at the insulator interface layer the surface may not be flat. As a result, some fault structures can provide higher binding energy sites to H, OH, and O. Similar to bulk material impurities, the surface can be modeled by a subset of sites that have different binding energies (and corresponding release rates, for example).

As an illustrative example, estimation can be performed in the following manner. There may be a relation between measurements (for example, resistance and capacitor voltage shift) and $H_2$ pressure above the sensor that can be estimated from a combination of physics and empirical data (for example, curve(s) or lookup table(s)) A sudden change in $H_2$ pressure can cause the measurement to change relatively slowly. The underlying process can be a non-equilibrium process in the sensor(s), and finite rates of flow can cause a settling time to reach steady state. With an appropriate choice of states (logarithmic in pressure, for instance), the lag response of the measurements can be modeled by a relatively small number of exponential decays. There can be, for example, two exponential responses—a slow and fast response. It may be preferable to address the fast response first.

Consider, for example, a simple model of a low-pass filter, with input x and output z, were z is given by the convolution of x with the filter input response h(t)—for example, the filter is Linear Time Invariant ("LTI"). In this example, the impulse response h is known, the output z is measured, and the input x is to be estimated. General approaches to this problem (for example, deconvolution filters), can employ a complex impulse response h (and thus causing a state that is large) and employ output z to smooth measurements previous in time to estimate input x vs. time given output z vs. time.

In this example, there are two special considerations: (1) only the current input (for example, the current pressure of $H_2$ is to be estimated and the importance of past measurements is of reduced significance; and (2) the impulse response h is simplified by modeling h using a relatively small number of poles (for example, 1 pole).

A single-pole low-pass filter (for example, an autoregressive filter) can be modeled in time as:

$$z_{k+1} = (1-a)z_k + a \cdot x_k$$

$$a = 1 - e^{-(t_{k+1} - t_k)/\tau}$$

where tau is the exponential (for example, autocorrelation) time constant of the filter (for example, "forgetting factor"). This recursion relation matches a convolution filter with an exponential impulse response h:

$$z_k = ax_k + (1-a)z_{k-1} = ax_k + (1-a)ax_{k-1} + (1-a)^2 ax_{k-2} + \ldots$$

$$z_k = \sum_{l=0}^{\infty} h_l x_{k-l} = \sum_{l=0}^{\infty} a(1-a)^l x_{k-l}$$

$$h_l = a(1-a)^l = ae^{-l\Delta t/\tau}$$

This assumes a constant time step $\Delta t$ for illustration, but also applies for variable time steps, as long as the forgetting factor τ is adjusted for new time steps. Also it should be noted that the filter has a gain of unity (for example, the sum of h is one). This approach can be extended to a plurality of exponential responses, but such complexity may not be necessary to obtain desired results.

For a given history of $z_k$, it is possible to estimate the current value of $x_k$. A length-2 state can provide the necessary behavior, and the state time update and measurement relation can be given by:

state at $t_k$:

$$\begin{Bmatrix} x_k \\ \Sigma_k \end{Bmatrix}$$

$$\Sigma_k \equiv a \sum_{l=0} x_{k-l} e^{-(t_k - t_{k-l})/\tau}$$

$$\begin{Bmatrix} x_{k+1} \\ \Sigma_{k+1} \end{Bmatrix} = \begin{Bmatrix} 1 & 0 \\ a & e^{-(t_{k+1}-t_k)/\tau} \end{Bmatrix} \begin{Bmatrix} x_k \\ \Sigma_k \end{Bmatrix}$$

These expressions may not yet reflect measurement noise, or dynamics of the system: for example, the current state $x_k$ can be mapped forward without change. In reality, the measurements will be noisy, and there will be some limit to the plausible rate that the input can change. Measurement noise can be added to the state according to:

$$\begin{Bmatrix} x_{k+1} \\ \Sigma_{k+1} \end{Bmatrix} = \begin{Bmatrix} 1 & 0 \\ a & 1-a \end{Bmatrix} \begin{Bmatrix} x_k \\ \Sigma_k \end{Bmatrix} + \begin{Bmatrix} \sigma_{x,rw} \\ 0 \end{Bmatrix} \hat{n}_{x,k}$$

$$z_k = \Sigma_k + \sigma_z \hat{n}_{z,k}$$

Here, measurement noise n(hat)$_z$ is added to the low-pass state, and can be additive white Gaussian noise with uncertainty/sigma_z (standard deviation) Other measurement errors, such as slowly varying offsets from circuit drift and imperfect modeling, will be addressed below.

The process noise (for example, the noise added to the current state term in the update equation), can have the form of a random walk, since the update estimate starts at the previous estimate and white noise uncertainty n(hat)$_{x,k}$ can be assumed from one time step to the next. The scale constant on the unit white process noise n(hat)$_{x,k}$ can be the random-walk uncertainty in units of state/sqrt(s), and can reflect the allowed change in the current state in a single time step (1-sigma).

The model can now be employed to estimate x from z using a Kalman filter approach:

$$\Phi = \begin{Bmatrix} 1 & 0 \\ a & 1-a \end{Bmatrix}$$

$$Q = \begin{Bmatrix} \sigma_{x,rw}^2 & 0 \\ 0 & 0 \end{Bmatrix}$$

$$\frac{\partial z}{\partial x} = \{0 \quad 1\}$$

$$R = \{\sigma_z^2\}$$

current state: $x_1$

Further developing this model, resistance R and capacitance voltage shift ΔV can be a function of internal sensor hydrogen concentrations: for example, R can depend on bulk material coverage $\theta_b$, and ΔV can depend on interface layer coverage $\theta_i$ (see above for a further discussion of θ). States of interest can include, for example, the partial pressure of $H_2$ and $O_2$ above the sensor ($pH_2$ and $pO_2$). For a given state [$pH_2$, $pO_2$], there may be known steady-state values of R and ΔV. It is assumed, for the sake of example, that this information is available or able to be estimated (for example, in a lookup table or other model). Further, for a given state [$pH_2$, $pO_2$] if the state suddenly changes, there may be known response times that are a function of the previous state to reach a new equilibrium. Using these assumptions:

$$\{R, \Delta V\} = \text{func}(\{pH_2, pO_2\}, \text{Temp})$$

and $$\tau_R, \tau_{\Delta V}(\{pH_2, pO_2\})$$

According to low-pass filtering modeling, the space chosen for the low-pass state can have an exponential behavior. In the case of the R measurement. The time update equation for a 1-pole update can be expressed by:

$$R_{k+1} = a_R R(pH_{2,k}, pO_{2,k}) + (1-a_R) R_k$$

where the state has 3 terms: $pH_2$, $pO_2$, and R, where $a_R$ is derived from $\tau_R$ of the current state. The covariance update can involve computation of the state transition matrix Φ. Given the estimate update expressed as $$x_{k+1} = x_k + \Delta x$$

The state transition matrix Φ can be given by:

$$\Phi = I + \frac{d\Delta x}{dx}$$

To determine the update of R, it can be given by:

$$\Delta R = R_{k+1} - R_k = a_R R(pH_{2,k}, pO_{2,k}) - a_R R_k$$

$$\frac{d\Delta R}{\{pH_{2,k}, pO_{2,k}, R_k\}} = \begin{Bmatrix} a_R \frac{dR}{dpH_2}(pH_{2,k}, pO_{2,k}), \\ a_R \frac{dR}{dpO_2}(pH_{2,k}, pO_{2,k}), -a_R \end{Bmatrix}$$

Accounting for the measurement of the capacitor voltage shift ΔV, the Kalman filter equations can be as follows. For the state estimate time update:

$$pH_{2,k+1} = pH_{2,k}$$

$$pO_{2,k+1} = pO_{2,k}$$

$$R_{k+1} = a_R R(pH_{2,k}, pO_{2,k}) + (1-a_R) R_k$$

$$\Delta V_{k+1} = a_{\Delta V} \Delta V(pH_{2,k}, pO_{2,k}) + (1-a_{\Delta V}) \Delta V_k$$

For the state covariance time update:

$$\Phi = \begin{Bmatrix} 1 & 0 & 0 & 0 \\ 0 & 1 & 0 & 0 \\ a_R \frac{dR}{dpH_2}(pH_{2,k}, pO_{2,k}) & a_R \frac{dR}{dpO_2}(pH_{2,k}, pO_{2,k}) & -a_R & 0 \\ a_{\Delta V} \frac{d\Delta V}{dpH_2}(pH_{2,k}, pO_{2,k}) & a_{\Delta V} \frac{d\Delta V}{dpO_2}(pH_{2,k}, pO_{2,k}) & 0 & -a_{\Delta V} \end{Bmatrix}$$

And for the measurement update, the filtered state terms of R and ΔV can be used.

Figure 6:
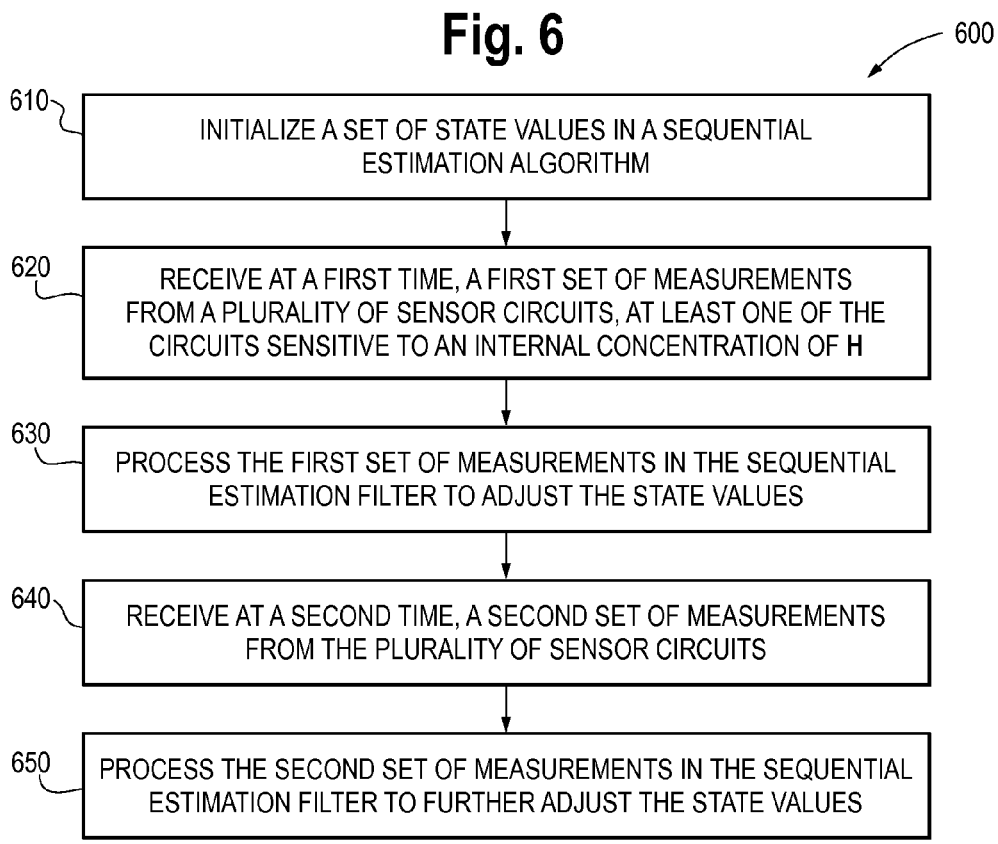
FIG. 6 shows a flow chart for measuring a pressure of one or more gasses, in accordance with an embodiment of the present system.

FIG. 6 shows a flow chart 600 for a method of chart for measuring a pressure of one or more gasses, in accordance with an embodiment of the present system. The steps of flow chart 600 can be performed, for example, by a system, such as system 100. Furthermore, the steps of method 600 can be performed in a different order, or some steps can be omitted according to design preferences. Method 600, or a portion thereof, can be performed by one or more processing units. Method 600, or a portion thereof, can be performed by software, hardware, and/or firmware. Method 600, or a portion thereof, can also be expressed through a set of instructions stored on one of more computer-readable storage media, such as RAM, ROM, EPROM, EEPROM, optical disk, magnetic disk, magnetic tape, and/or the like.

At step 610, a set of state values in a sequential estimation filter is initialized. At step 620, a first set of measurements from a plurality of sensors is received, where at least one of the sensors is sensitive to an internal concentration of H. At step 630, the first set of measurements in the sequential estimation filter is processed to adjust the state values. At step 640, a second set of measurements from a plurality of sensors is received, where at least one of the sensors is sensitive to an internal concentration of H. At step 650, the second set of measurements in the sequential estimation filter is processed to adjust the state values.

To illustrate an example, flow chart 600 can be implemented in the following manner. At step 610, measurements are received from one or more sensors (for example, sensors 200). The received measurements include a resistance measurement from a resistive sensor (for example, sensor 210), a capacitive sensor (for example, sensor 220), and a temperature sensor (for example, sensor 250). Both the resistive and capacitive sensors are sensitive to internal concentrations of H (for example, as discussed above with respect to FIGS. 3 and 4).

At step 630, the resistance, capacitance, and temperature are processed using a 5-state Kalman filter.

While particular steps, elements, embodiments and applications of the present invention have been shown and described, it will be understood, of course, that the invention is not limited thereto since modifications can be made by those skilled in the art, particularly in light of the foregoing teachings.

What is claimed is:

1. A system for estimating gas concentrations in a mixed atmosphere, the system comprising:
   a plurality of sensors, wherein each of the plurality of sensors is configured to provide data representative of a presence of a first gas and a second gas in the mixed atmosphere, and wherein the data from each of the plurality of sensors forms a set of measurements;
   a processor configured to:
      receive said set of measurements;
      execute a sequential estimation filter comprising a plurality of states, said plurality of states having a corresponding set of values; and
      adjust at least a portion of said set of values in response to said set of measurements; and
   wherein:
      at least one of said set of values represents a concentration of the first gas in the mixed atmosphere; and
      at least one of said set of values represents a concentration of the second gas in the mixed atmosphere.

2. The system of claim 1, wherein said plurality of sensors comprises a resistive sensor and a capacitive sensor.

3. The system of claim 2, wherein said plurality of states comprises states representative of a hydrogen pressure in the mixed atmosphere, a concentration of hydrogen in a bulk material of at least one of said sensors, and a concentration of hydrogen in an interface layer of at least one of said sensors.

4. The system of claim 3, wherein said plurality of states further comprises states representative of a concentration of oxygen on a surface of one of said sensors, and an oxygen pressure in the mixed atmosphere.

5. The system of claim 2, wherein said plurality of sensors further comprises a temperature sensor.

6. The system of claim 1, wherein at least a portion of said set of values is initialized.

7. The system of claim 1, wherein said sequential estimation filter comprises a Kalman filter.

8. The system of claim 1, wherein the first gas comprises Hydrogen.

9. The system of claim 8, wherein the second gas comprises Oxygen.

10. A method for estimating gas concentrations in a mixed atmosphere, the method comprising:
    receiving at a first time, a first set of measurements from a plurality of sensors, wherein each of said first set of measurements includes information corresponding to a presence of a first gas and a second gas in the mixed atmosphere;
    processing said first of said set of measurements in a sequential estimation filter to adjust a set of state values;
    receiving at a second time a second set of measurements from said plurality of sensors, wherein each of said second set of measurements includes information corresponding to a presence of said first gas and said second gas in the mixed atmosphere;
    processing said second of said set of measurements in said sequential estimation filter to further adjust said set of state values; and
    wherein:
       at least one of said set of values represents a concentration of the first gas in the mixed atmosphere; and
       at least one of said set of values represents a concentration of the second gas in the mixed atmosphere.

11. The method of claim 10, wherein said plurality of sensors comprises a resistive sensor and a capacitive sensor.

12. The method of claim 11, wherein said set of state values comprises values representative of a hydrogen pressure in the mixed atmosphere, a concentration of hydrogen in a bulk material of at least one of said sensors, and a concentration of hydrogen in an interface layer of at least one of said sensors.

13. The method of claim 12, wherein said set of state values further comprises values representative of a concentration of oxygen on a surface of at least one of said sensors, and an oxygen pressure in the mixed atmosphere.

14. The method of claim 11, wherein said plurality of sensors further comprises a temperature sensor.

15. The method of claim 10, wherein at least a portion of said state values comprises initial state values.

16. The method of claim 10, wherein said sequential estimation filter comprises a Kalman filter.

17. The method of claim 10, wherein said set of state values comprises at least five state values.

18. The method of claim 17, wherein said at least five state values comprise values representative of a hydrogen pressure in the mixed atmosphere, a concentration of hydrogen in a bulk material of at least one of said sensors, and a concentration of hydrogen in an interface layer of at least one of said sensors, a concentration of oxygen on a surface of at least one of said sensors, and an oxygen pressure in the mixed atmosphere.

19. The method of claim 10, wherein the first gas comprises Hydrogen.

20. The method of claim 19, wherein the second gas comprises Oxygen.

* * * * *